(12) United States Patent
Satoh

(10) Patent No.: US 6,755,848 B2
(45) Date of Patent: Jun. 29, 2004

(54) LIGHT-RAY THERAPEUTIC APPARATUS

(75) Inventor: Taiji Satoh, Saitama (JP)

(73) Assignee: Seric Ltd., Tokyo (JP)

(*) Notice: Subject to any disclaimer, the term of this patent is extended or adjusted under 35 U.S.C. 154(b) by 27 days.

(21) Appl. No.: 10/096,386

(22) Filed: Mar. 12, 2002

(65) Prior Publication Data

US 2002/0133212 A1 Sep. 19, 2002

(30) Foreign Application Priority Data

Mar. 13, 2001 (JP) ........................................ 2001-070327

(51) Int. Cl.[7] ............................................. A61N 5/006
(52) U.S. Cl. ............................. 607/88; 607/91; 607/94; 606/3; 606/10; 606/13; 606/17; 606/18
(58) Field of Search ........................ 607/88–91, 93–96; 606/3, 10, 11, 17, 18

(56) References Cited

U.S. PATENT DOCUMENTS

| | | | | |
|---|---|---|---|---|
| 2,469,412 A | * | 5/1949 | Roebken | 128/396 |
| 2,510,017 A | * | 5/1950 | Furedy et al. | 250/36 |
| 2,954,771 A | * | 10/1960 | Boyan | 128/396 |
| 3,662,175 A | * | 5/1972 | Davidson et al. | 250/86 |
| 4,298,005 A | * | 11/1981 | Mutzhas | 128/396 |
| 5,591,219 A | * | 1/1997 | Dungan | 607/88 |
| 5,707,401 A | * | 1/1998 | Talmore | 607/88 |
| 5,843,143 A | * | 12/1998 | Whitehurst | 607/88 |
| 5,849,026 A | * | 12/1998 | Zhou et al. | 607/90 |
| 6,280,438 B1 | * | 8/2001 | Eckhouse et al. | 606/9 |
| 6,413,268 B1 | * | 7/2002 | Hartman | 607/94 |

* cited by examiner

*Primary Examiner*—Linda C. M. Dvorak
*Assistant Examiner*—Ahmed Farah
(74) *Attorney, Agent, or Firm*—Pitney, Hardin, Kipp & Szuch LLP

(57) ABSTRACT

A light-ray therapeutic apparatus having: a xenon illuminating lamp including a lamp body, a lamp holder provided in the lamp body, a xenon lamp held by the lamp holder, a reflecting mirror for reflecting light emitted from the xenon lamp, and a multilayer film coating-type spectral correction filter provided in a front portion of the lamp body; wherein, of the light from the xenon lamp, energy of ultraviolet rays having a wavelength not longer than 280 nm is cut off by the spectral correction filter, and spectral coincidence in an ultraviolet wavelength range of 280–400 nm, in a visible wavelength range of 380–780 nm, and in an infrared wavelength range of 780–2,500 nm are made 100±30% respectively, while the spectral coincidence is defined as a ratio of relative energy distribution of the light of the xenon lamp to relative energy distribution of the reference sunlight.

4 Claims, 6 Drawing Sheets

SPECTRAL DISTRIBUTION OF XENON ILLUMINATING LAMP AND SUNLIGHT

| RELATIVE ENERGY COINCIDENCE | | | |
|---|---|---|---|
| WAVELENGTH RANGE | RELATIVE ENERGY DISTRIBUTION OF XENON ILLUMINATING LAMP (%) | RELATIVE ENERGY DISTRIBUTION OF SUNLIGHT (%) | COINCIDENCE (%) |
| 280-400 nm | 6.0 | 6.2 | 97 |
| 380-780 nm | 49.0 | 52.5 | 93 |
| 780-2500 nm | 47.0 | 43.2 | 109 |

[NOTE] The relative energy distribution of sunlight in this table was defined on the basis of the recommendation (TC-2.2,1972) for integrated irradiance of simulated solar radiation source for testing purposes according to International Commission on Illumination (CIE), as follows. That is, the wavelength range of from 280 nm to 2,500 nm was divided into an ultraviolet range (wavelength from 280 nm to 400 nm), a visible range (wavelength from 380 nm to 780 nm) and an infrared range (wavelength from 780 nm to 2,500 nm), and integrated values in the respective range were calculated.

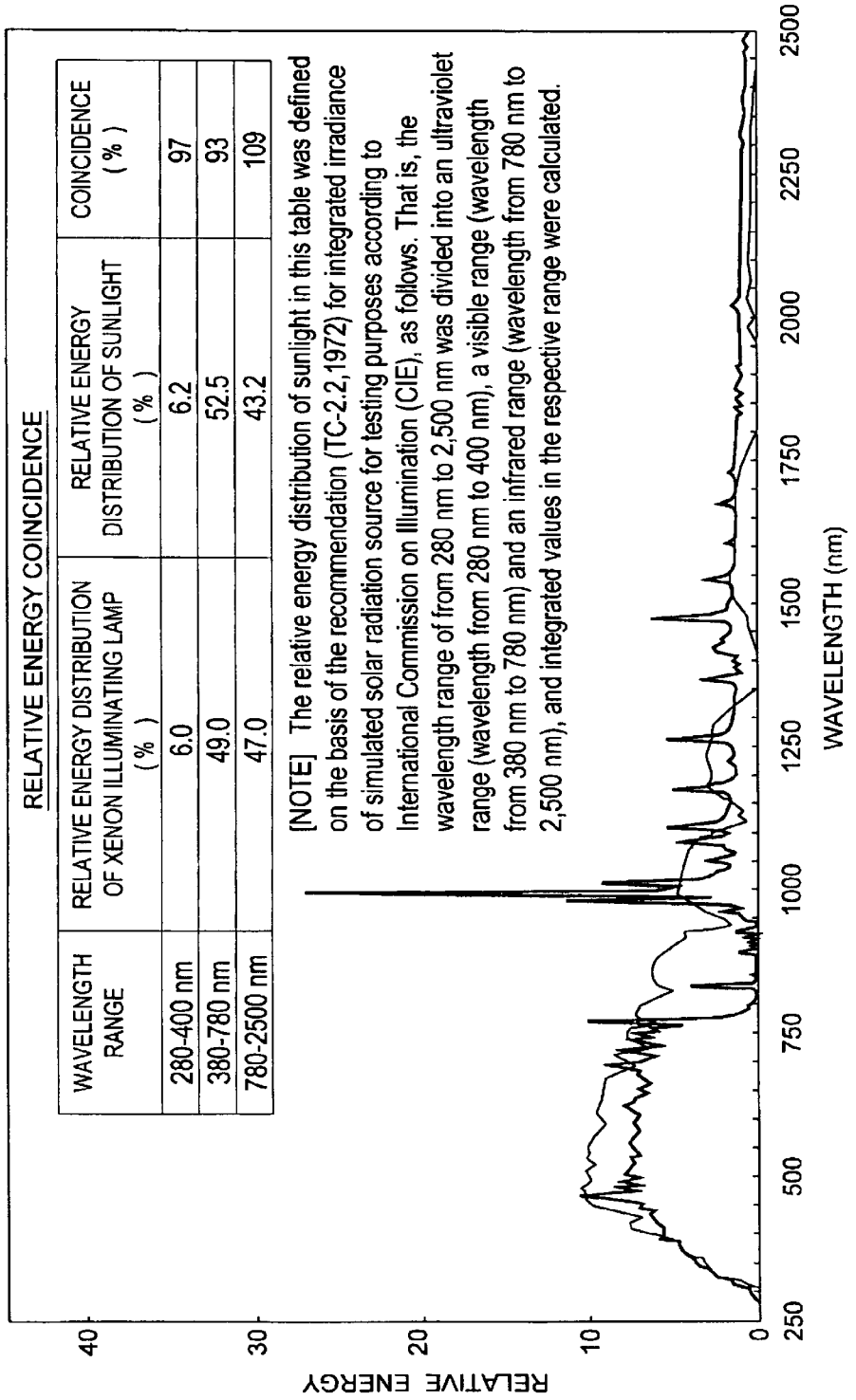
F I G. 6

LIGHT-RAY THERAPEUTIC APPARATUS

BACKGROUND OF THE INVENTION

1. Field of the Invention

The present invention relates to a light-ray therapeutic apparatus, and particularly relates to a light-ray therapeutic apparatus suitable for treating decubitus ulcers.

2. Related Art of the Invention

Sacral regions, greater trochanteric regions, calcaneal regions, and so on, of patients unavoidably laid up for a long time are constricted persistently so that blood circulation is locally stopped. Thus, such regions are apt to become decubitus ulcers. Such decubitus ulcers are very difficult to treat because tissue becomes necrotic.

It has been known since early times that the healing of decubitus ulcers is accelerated if the decubitus ulcers are irradiated with sunlight. However, the sunlight depends on weather and changes in accordance with time. In addition, it is sometimes difficult for sunlight to enter a room. Thus, there have been drawbacks in making use of sunlight for actual therapy.

On the other hand, it has been known that light rays from a xenon lamp have spectral distribution close to that of sunlight. However, the light rays emitted from the xenon lamp have some defects as follows.

1. Harmful ultraviolet rays with a wavelength of not longer than 280 nm are included. Such ultraviolet rays indeed have a strong bactericidal action but have a damaging effect on skin.
2. Excessive heat is generated by near infrared rays. Thus, irradiation cannot be carried out over a long period of time. In addition, it is difficult and dangerous to handle the light.
3. There are a large quantity of bright line spectra peculiar to the xenon lamp.

SUMMARY OF THE INVENTION

It is therefore an object of the present invention to provide a light-ray therapeutic apparatus which has a therapeutic effect equivalent to that of sunlight; which does not depend on weather or time and can be used easily and for any desired period of time; which has no damaging effect on skin; and which is suitable particularly for therapy of decubitus ulcers or the like.

In order to solve the problems, the invention provides a light-ray therapeutic apparatus having: a xenon illuminating lamp including a lamp body, a lamp holder provided in the lamp body, a xenon lamp held by the lamp holder, a reflecting mirror for reflecting light emitted from the xenon lamp, and a multilayer film coating-type spectral correction filter provided in a front portion of the lamp body; wherein, of light emitted from the xenon lamp, energy of ultraviolet rays with a wavelength of not longer than 280 nm is cut off perfectly by the spectral correction filter, and spectral coincidence in an ultraviolet wavelength range of 280–400 nm, spectral coincidence in a visible wavelength range of 380–780 nm, and spectral coincidence in an infrared wavelength range of 780–2,500 nm are made 100±30% respectively, while the spectral coincidence is defined as a ratio of relative energy distribution of the light of the xenon illuminating lamp to relative energy distribution of the reference sunlight.

In the light-ray therapeutic apparatus according to the invention, of rays radiated from the xenon lamp having a wavelength distribution close to that of sunlight rays, harmful ultraviolet rays with a wavelength of not longer than 280 nm are cut off by the multilayer film coating-type spectral correction filter. Accordingly, the strong bactericidal action is avoided so that there is no fear of damaging the skin. Further, the spectral coincidence is made 100±30% in all the above-mentioned wavelength bands so that rays closely approximating to sunlight can be obtained. Excessive heat generation in irradiation with the rays is prevented, and a large quantity of bright line spectra peculiar to the xenon lamp are suppressed. Thus, the light-ray therapeutic apparatus according to the invention can be used as alternative light for obtaining equivalent medical efficacy to the sunlight. In addition, the light-ray therapeutic apparatus according to the invention does not depend on weather or time and allows therapy at any time and for any desired period of time. Further, the light-ray therapeutic apparatus according to the invention allows ease of use and indoor therapy.

Further, preferably, the spectral correction filter is constituted by a glass substrate, and indium oxide, aluminum oxide, tin oxide, magnesium fluoride, etc. deposited in multi-layers on the glass substrate, so that rays of the xenon lamp having the aforementioned spectral characteristic can be obtained.

Further, preferably, being attached to a stand, the xenon illuminating lamp is attached to a stand adjustable in height and adjustable in irradiation angle, and irradiation time can be controlled by a timer, so that the irradiated energy of the rays can be adjusted.

BRIEF DESCRIPTION OF THE DRAWINGS

FIG. 6 is a graph showing an example of the spectral characteristic of the xenon illuminating lamp corrected by the spectral correction filter, in comparison with the spectral characteristic of sunlight.

DESCRIPTION OF THE PREFERRED EMBODIMENT

Next, a light-ray therapeutic apparatus according to an embodiment of the invention will be described in detail with reference to the drawings.

Figure 1:
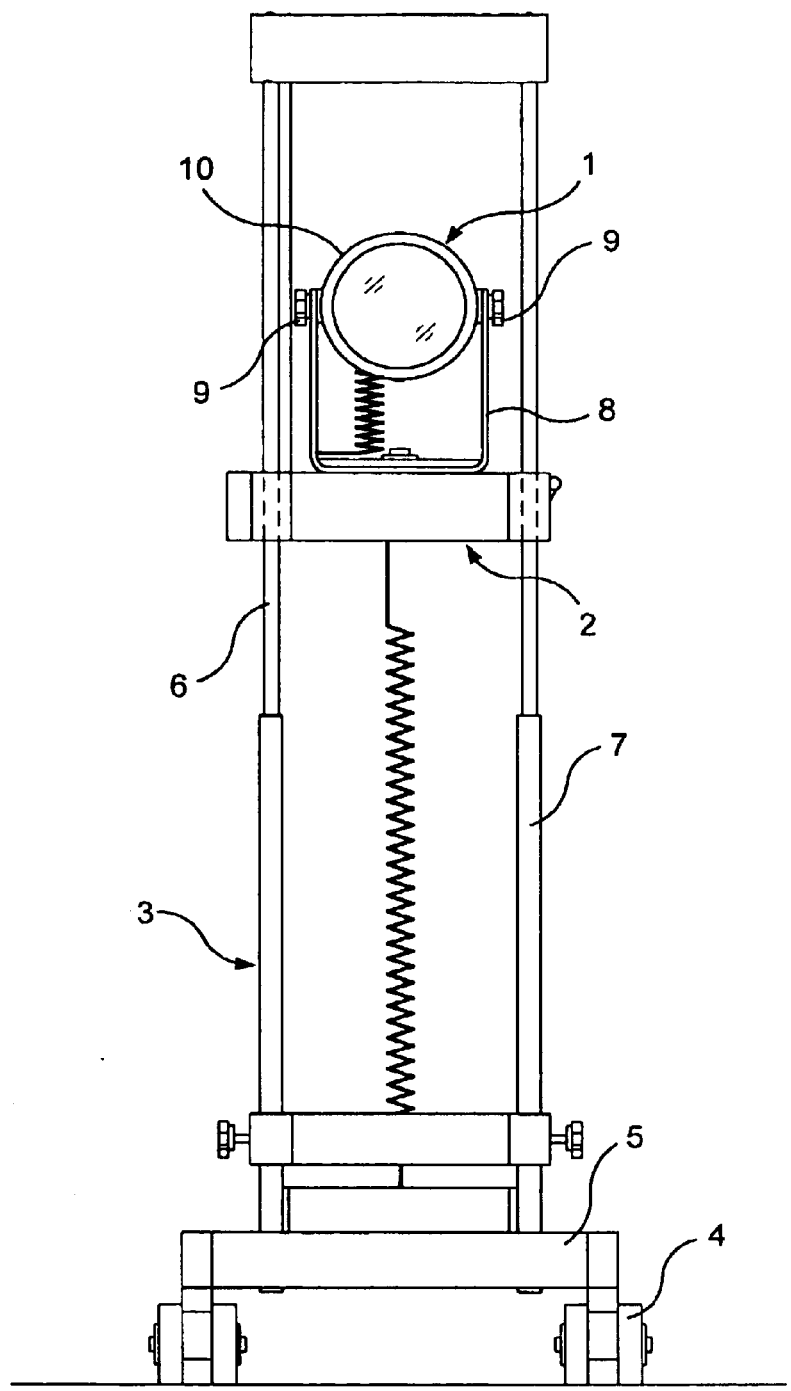
FIG. 1 is a front view of a light-ray therapeutic apparatus according to an embodiment of the invention.
Figure 2:
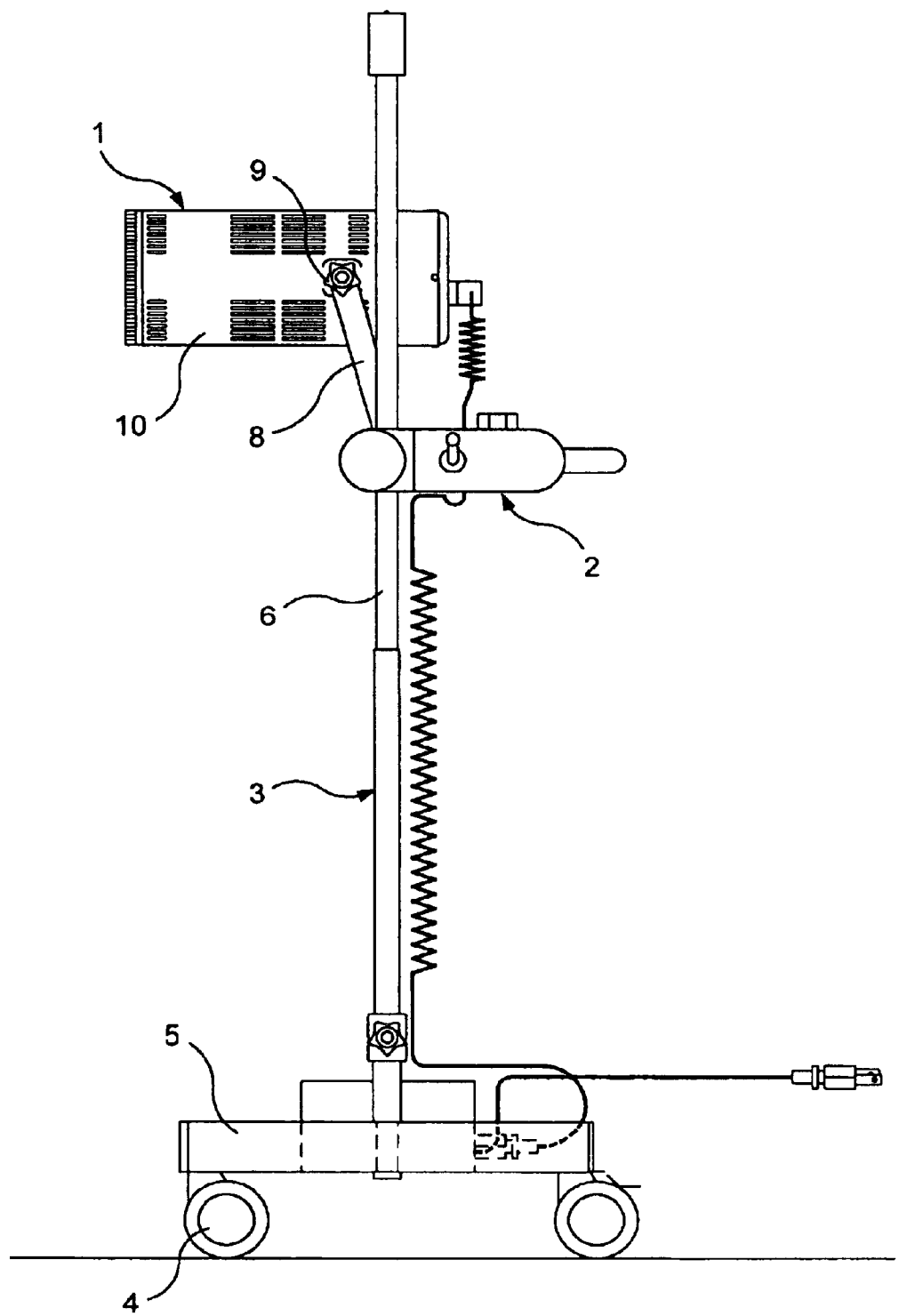
FIG. 2 is a side view of the light-ray therapeutic apparatus in FIG. 1.

FIG. 1 shows a front view of the light-ray therapeutic apparatus according to the embodiment of the invention, and FIG. 2 shows a side view thereof. The light-ray therapeutic apparatus is constituted by a xenon illuminating lamp 1, a control box 2 for controlling the xenon illuminating lamp 1, and a stand 3 for supporting the xenon illuminating lamp 1 and the control box 2. This stand 3 has a pedestal 5 which can be moved by use of casters 4, and two supports 6 and 7 fixed onto this pedestal. The control box 2 is attached to the supports 6 and 7 horizontally. The control box 2 has a lighting switch and a timer (both not shown).

Figure 3:
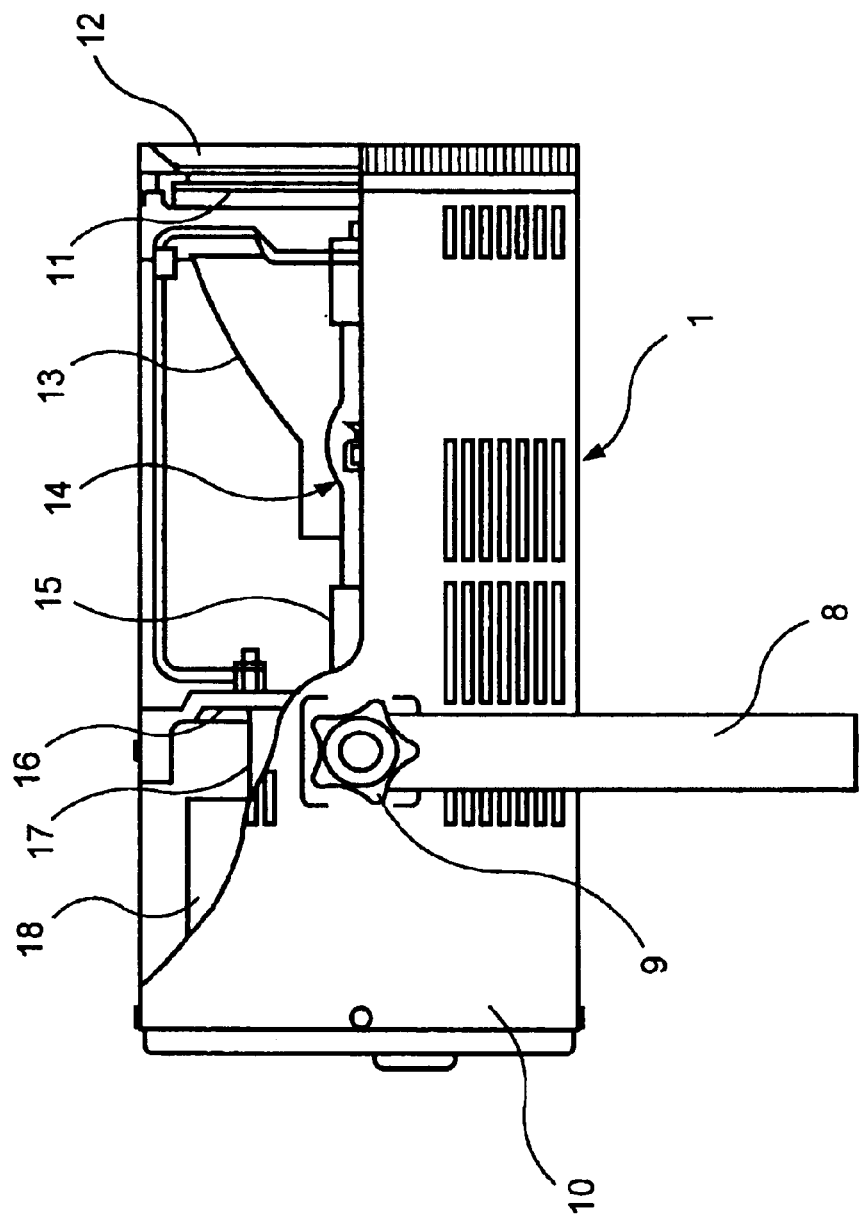
FIG. 3 is a partially broken side view of a xenon illuminating lamp of the light-ray therapeutic apparatus.

The xenon illuminating lamp assembly 1 is attached to the upper ends of a U-shaped arm 8, which is fixed to the control box 2, through clamp knobs 9 so that the angle of the xenon illuminating lamp 1 can be adjusted. As shown in FIG. 3, the xenon illuminating lamp assembly 1 is provided with a cylindrical lamp body 10, having a large number of air guide slits in its outer circumferential surface and its rear end surface. The front side of the lamp body 10 is made open. A front frame 12 with a spectral correction filter 11 having a multilayer film coating structure is attached to the open front side of the lamp body 10 by screws. A reflecting mirror 13 is disposed behind the filter 11, and a xenon lamp 14 as a light source for continuously emitting light is disposed at the center of the reflecting mirror 13. The xenon lamp 14 is held by a lamp holder 15.

The cylindrical lamp body 10 has a partition plate 16 substantially at its center. A starter 17, a power supply unit 18 and so on are disposed at the rear of the partition plate.

Figure 4:
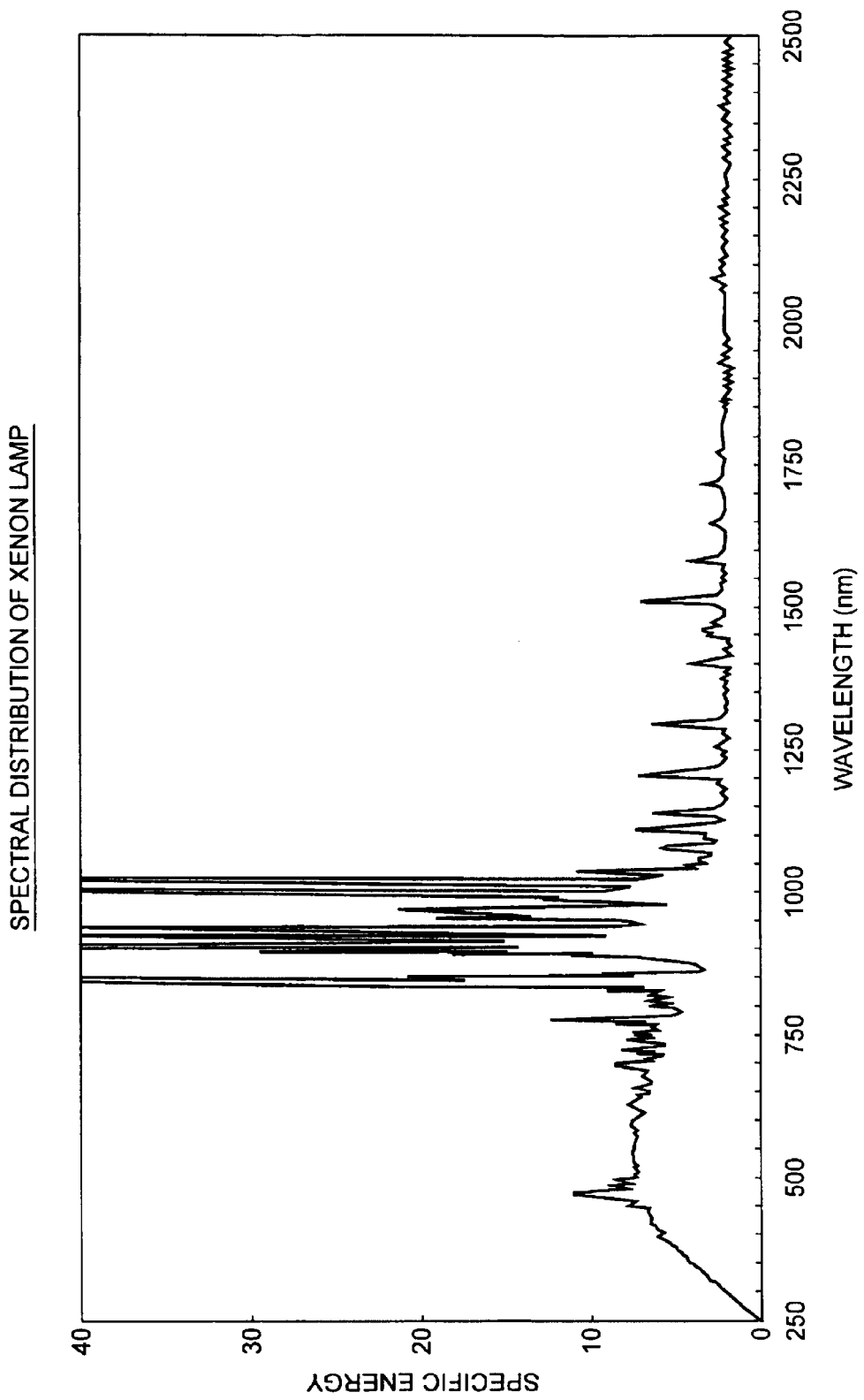
FIG. 4 is a graph showing an example of the spectral characteristic of light emitted from a xenon lamp and not subjected to spectral correction.

FIG. 4 shows a typical example of the spectral characteristic of light emitted from the xenon lamp 14, that is, the spectral characteristic of light which has not been corrected by the spectral correction filter 11. As is understood from FIG. 4, the light emitted from the xenon lamp 14 has harmful ultraviolet rays with the wavelength range of not longer than 280 nm. In addition, a large quantity of bright line spectra peculiar to the xenon lamp exist in the infrared range of 800–1,050 nm. Further, near infrared rays generate excessive heat.

Figure 5:
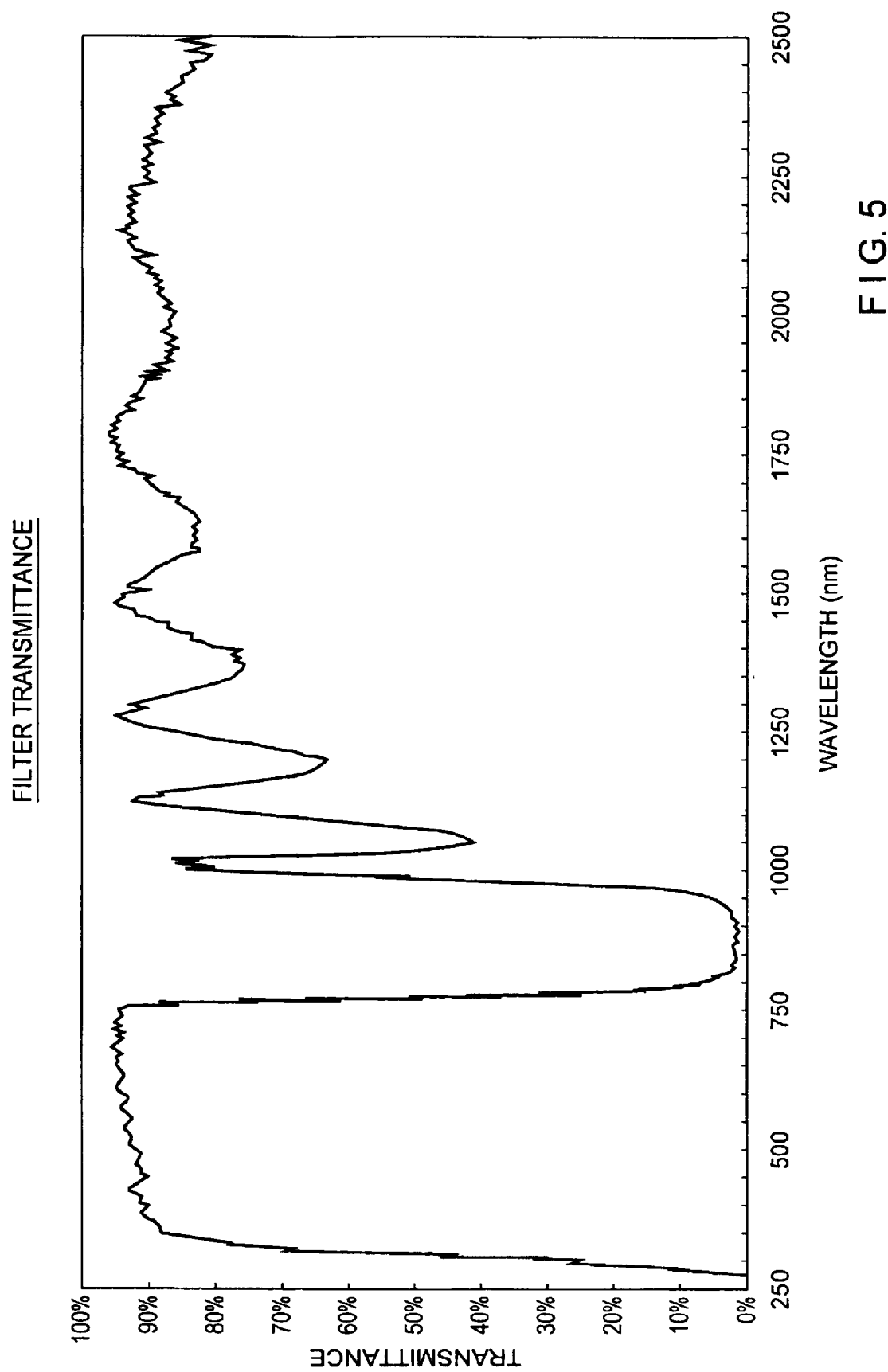
FIG. 5 is a graph showing an example of the transmittance of a spectral correction filter.

The spectral correction filter 11 for selectively transmitting the light from the xenon lamp 14 in accordance with wavelength has a multilayer film coating structure in which indium oxide, aluminum oxide, tin oxide, magnesium fluoride, etc., have been deposited in multi-layers on a glass substrate. FIG. 5 shows an example of the transmittance of the spectral correction filter 11. As is understood from this graph, the spectral correction filter 11 has low transmittance in the ultraviolet range of particularly not longer than 300 nm and in the infrared range of 800–950 nm, and high transmittance in the visible range. Incidentally, the above-mentioned spectral characteristic and transmittance can be measured by a spectrophotometer.

FIG. 6 shows an example of the spectral characteristic of the light of the xenon illuminating lamp corrected by the spectral correction filter 11 together with the spectral characteristic of sunlight. In this case, it is important that, of the irradiated light from the xenon illuminating lamp, the energy of ultraviolet rays with a wavelength of not longer than 280 nm is cut off perfectly, and spectral coincidence in the ultraviolet wavelength range of 280–400 nm, spectral coincidence in the visible wavelength range of 380–780 nm, and spectral coincidence in the infrared wavelength range of 780–2,500 nm are made 100±30% respectively, while the spectral coincidence is defined as the ratio of the relative energy distribution of the light of the xenon illuminating lamp to the relative energy distribution of the reference sunlight. An example of such spectral coincidence is shown in the table in FIG. 6. In this example, the relative energy distribution of the reference sunlight in the wavelength range of 280–400 nm, that in the wavelength range of 380–780 nm, and that in the wavelength range of 780–2,500 nm are 6.2%, 52.5% and 43.2% respectively. On the other hand, the relative energy distribution of the light of the xenon illuminating lamp in the wavelength range of 280–400 nm, that in the wavelength range of 380–780 nm, and that in the wavelength range of 780–2,500 nm are 6.0%, 49.0% and 47.0% respectively. Thus, the spectral coincidence in the wavelength range of 280–400 nm is 6.0÷6.2×100=97%, that in the wavelength range of 380–780 nm is 49.0÷52.5×100=93%, and that in the wavelength range of 780–2,500 nm is 47.0÷43.2×100=109%.

By setting the spectral characteristic of the light of the xenon illuminating lamp as described above, it is possible to obtain a spectral characteristic in which harmful ultraviolet rays have been removed and excessive bright line spectra have been reduced so that the spectral characteristic approximates that of sunlight. Thus, according to this light, in the same manner as sunlight, ultraviolet rays sterilize superficial fungus, and visible rays and infrared rays penetrate up to a deep layer of texture so as to activate cell functions, while all the rays in the wavelength bands act synergistically to accelerate skin regeneration and stimulate granulation cells and new blood vessels to form. Thus, it is apparent that this light is effective in light-ray therapy, particularly in treating decubitus ulcers.

Further, since the irradiated light from the xenon illuminating lamp does not contain ultraviolet rays with a wavelength of not longer than 280 nm, there is no strong bactericidal action or no influence on cells. Further, as a result of measuring irradiated energy from the xenon illuminating lamp, it was proved that the irradiated energy was substantially in inverse proportion to the square of the irradiation distance and in proportion to the irradiation time. To perform effective therapy, the irradiated energy should be increased (the irradiation distance is reduced, and the irradiation time is prolonged). However, to avoid side effects such as scalds caused by radiant heat or erythema and the like caused by ultraviolet rays, it is desired that the irradiation distance be set appropriately, for example, at 70 cm, and the irradiation time per round of irradiation be set, for example, at 30 minutes.

By use of a xenon illuminating lamp of an XC-100BM type (100 W) by the present inventor, the therapeutic gain on decubitus ulcers was verified. The second or higher degrees of decubitus ulcers were targeted, and irradiated with rays from the xenon illuminating lamp at an irradiation distance of 70 cm for 30 minutes per time. Such irradiation was carried out three times a day. The therapeutic gain was determined as follows. The reduction ratio of the residual area of each decubitus ulcer after passage of three months was calculated. The therapeutic gain was determined to be complete response when the reduction ratio was lower than 30%, partial response when the reduction ratio was not lower than 30% and lower than 60%, minor response when the reduction ratio was not lower than 60% and lower than 80%, and no response when the reduction ratio was not lower than 80%. To remove any other causal relationship from the therapy, only the light-ray therapy as carried out without using any medicine except isodine for disinfection. In a comparative group, light-ray therapy was not carried out, and conventional therapy (disinfection, ointment application, pasting of wound dressing, and so on) was carried out on the decubitus ulcer.

As a result, not only complete healing of secondary infection but also development of pellicles and granulations in focal surfaces and further regeneration of healthy skin tissue from the periphery were observed. Thus, the existence of activation of cell functions and the existence of synthetic action of skin tissue were suggested as the focus healing mechanism. As to the therapeutic gain on the decubitus ulcer, of 64 cases in the clinical trial, 34 cases were complete response, 15 cases were partial response, 4 cases were minor response, and 11 cases were no response. In the comparative group, of 19 cases, 4 cases were complete response, 1 case was partial response, 2 cases were minor response, and 12 cases were no response. The efficacy ratio merging the cases for the complete response and the partial response was 76.5% in the clinical trial and 26.4% in the comparative group. As a result, it can be said that the therapy of decubitus ulcers using the xenon illuminating lamp is an extremely effective method.

It was further proved that the light-ray therapeutic apparatus according to the invention had therapeutic gain also in atopic dermatitis.

What is claimed is:

1. A light-ray therapeutic apparatus comprising:

a xenon illuminating lamp including a lamp body, a lamp holder provided in said lamp body, a xenon lamp held by said lamp holder, a reflecting mirror for reflecting light emitted from said xenon lamp, and a multilayer film coating-type spectral correction filter provided in a front portion of said lamp body;

wherein, of light emitted from said xenon lamp, energy of ultraviolet rays with a wavelength of not longer than 280 nm is cut off perfectly by said spectral correction filter, and spectral coincidence in an ultraviolet wavelength range of 280–400 nm, spectral coincidence in a visible wavelength range of 380–780 nm, and spectral coincidence in an infrared wavelength range of 780–2,500 nm are made 100±30% respectively, while the spectral coincidence is defined as a ratio of relative energy distribution of light of said xenon illuminating lamp to relative energy distribution of reference sunlight.

2. A light-ray therapeutic apparatus according to claim 1, wherein said xenon illuminating lamp being attached to a stand is adjustable in height and adjustable in irradiation angle, and irradiation time can be controlled by a timer.

3. A light-ray therapeutic apparatus according to claim 1, wherein said spectral correction filter (11) is constituted by a glass substrate, and indium oxide, aluminum oxide, tin oxide, or magnesium fluoride deposited in multi-layers on said glass substrate.

4. A light-ray therapeutic apparatus according to claim 2, wherein said xenon illuminating lamp being attached to a stand is adjustable in height and adjustable in irradiation angle, and irradiation time can be controlled by a timer.

* * * * *